(12) United States Patent
Hoshi

(10) Patent No.: US 11,166,680 B2
(45) Date of Patent: Nov. 9, 2021

(54) X-RAY CT SYSTEM AND MEDICAL BED APPARATUS

(71) Applicant: CANON MEDICAL SYSTEMS CORPORATION, Otawara (JP)

(72) Inventor: Naoto Hoshi, Nasu (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 238 days.

(21) Appl. No.: 16/417,301

(22) Filed: May 20, 2019

(65) Prior Publication Data
US 2019/0357860 A1    Nov. 28, 2019

(30) Foreign Application Priority Data

May 22, 2018 (JP) .............................. JP2018-098047

(51) Int. Cl.
*A61B 6/04* (2006.01)
*A61B 6/03* (2006.01)
*A61G 7/018* (2006.01)
*A61B 6/10* (2006.01)

(52) U.S. Cl.
CPC ............ *A61B 6/0407* (2013.01); *A61B 6/035* (2013.01); *A61B 6/0487* (2020.08); *A61B 6/102* (2013.01); *A61G 7/018* (2013.01); *A61G 2210/50* (2013.01)

(58) Field of Classification Search
CPC ....... A61B 6/032; A61B 6/035; A61B 6/0407; A61B 6/0487; A61B 6/44; A61B 6/54; A61B 6/102; A61G 7/018; A61G 2210/50
See application file for complete search history.

(56) References Cited

U.S. PATENT DOCUMENTS

| | | | | |
|---|---|---|---|---|
| 4,034,224 A | * | 7/1977 | Heavens | A61B 6/0428 378/20 |
| 4,771,785 A | * | 9/1988 | Duer | B66F 7/0608 600/415 |
| 4,910,819 A | * | 3/1990 | Brown | A61G 7/0502 378/209 |
| 5,066,915 A | * | 11/1991 | Omori | G01R 33/543 324/318 |
| 5,210,893 A | * | 5/1993 | Uosaki | A61B 5/055 5/601 |
| 5,475,885 A | | 12/1995 | Ishikawa | |
| 5,600,858 A | * | 2/1997 | Baer | A61B 6/0442 5/601 |
| 6,840,673 B2 | * | 1/2005 | Moritake | A61B 6/035 378/196 |

(Continued)

FOREIGN PATENT DOCUMENTS

| | | |
|---|---|---|
| JP | 6-133965 | 5/1994 |
| JP | WO2010/123024 A1 | 10/2010 |
| JP | 2016-63900 | 4/2016 |

*Primary Examiner* — David R Hare
(74) *Attorney, Agent, or Firm* — Oblon, McClelland, Maier & Neustadt, L.L.P.

(57) ABSTRACT

An X-ray CT system according to one embodiment includes a top plate on which a subject is laid, a driver configured to drive the top plate in a lateral direction of the top plate, a frame provided on both sides of the top plate in the lateral direction, and a cover provided between the frame and the top plate, respectively. The top plate and the cover are arranged so that the top plate does not come in contact with the cover in a drive range of the top plate by the driver in the lateral direction.

15 Claims, 9 Drawing Sheets

(56) References Cited

U.S. PATENT DOCUMENTS

| | | | |
|---|---|---|---|
| 6,955,464 B1 * | 10/2005 | Tybinkowski | A61B 6/0487 378/209 |
| 7,017,209 B1 * | 3/2006 | De Jong | A61B 6/0442 378/20 |
| 7,874,030 B2 * | 1/2011 | Cho | G01R 33/481 5/601 |
| 8,578,529 B2 | 11/2013 | Miyano et al. | |
| 10,159,449 B2 * | 12/2018 | Shang | B29C 70/443 |
| 10,295,619 B2 * | 5/2019 | Oosawa | G01R 33/30 |
| 2012/0023671 A1 | 2/2012 | Miyano et al. | |

* cited by examiner

X-RAY CT SYSTEM AND MEDICAL BED APPARATUS

CROSS-REFERENCE TO RELATED APPLICATIONS

This application is based upon and claims the benefit of priority from Japanese Patent Application No. 2018-098047, filed on May 22, 2018; the entire contents of which are incorporated herein by reference.

FIELD

Embodiments of the present invention relate to an X-ray CT system and a medical bed apparatus.

BACKGROUND

Among X-ray computed tomography (CT) systems, there are X-ray CT systems which may include a medical bed apparatus configured to convey a subject (a patient) to an X-ray irradiation gantry apparatus. This medical bed apparatus may include an external unit configured to drive the whole apparatus right and left, so that a position of a tomography target can be adjusted without moving the subject. In this case, it is necessary to drive the whole medical bed apparatus, and hence, a large drive force is required. Therefore, time and labor for remodeling and cost burdens increase.

DETAILED DESCRIPTION

In a medical bed apparatus, time and labor for remodeling and cost burdens can be suppressed, when a top plate on which a subject is laid can only be driven right and left. However, in the medical bed apparatus, a cover is generally provided between the top plate and a frame. Therefore, when the top plate is driven right and left, there is possibility that safety during the drive of the top plate becomes insufficient due to interference between the top plate and the cover.

An object of the present embodiment is to provide an X-ray CT system and a medical bed apparatus in which safety during drive of a top plate can be sufficiently secured.

An X-ray CT system according to the present embodiment includes a top plate on which a subject is laid, a driver configured to drive the top plate in a lateral direction of the top plate, a frame provided on both sides of the top plate in the lateral direction, and a cover provided between the frame and the top plate, respectively. The top plate and the cover are arranged so that the top plate does not come in contact with the cover in a drive range of the top plate by the driver in the lateral direction.

Embodiments will now be explained with reference to the accompanying drawings. The present invention is not limited to the embodiments.

First Embodiment

Figure 1:
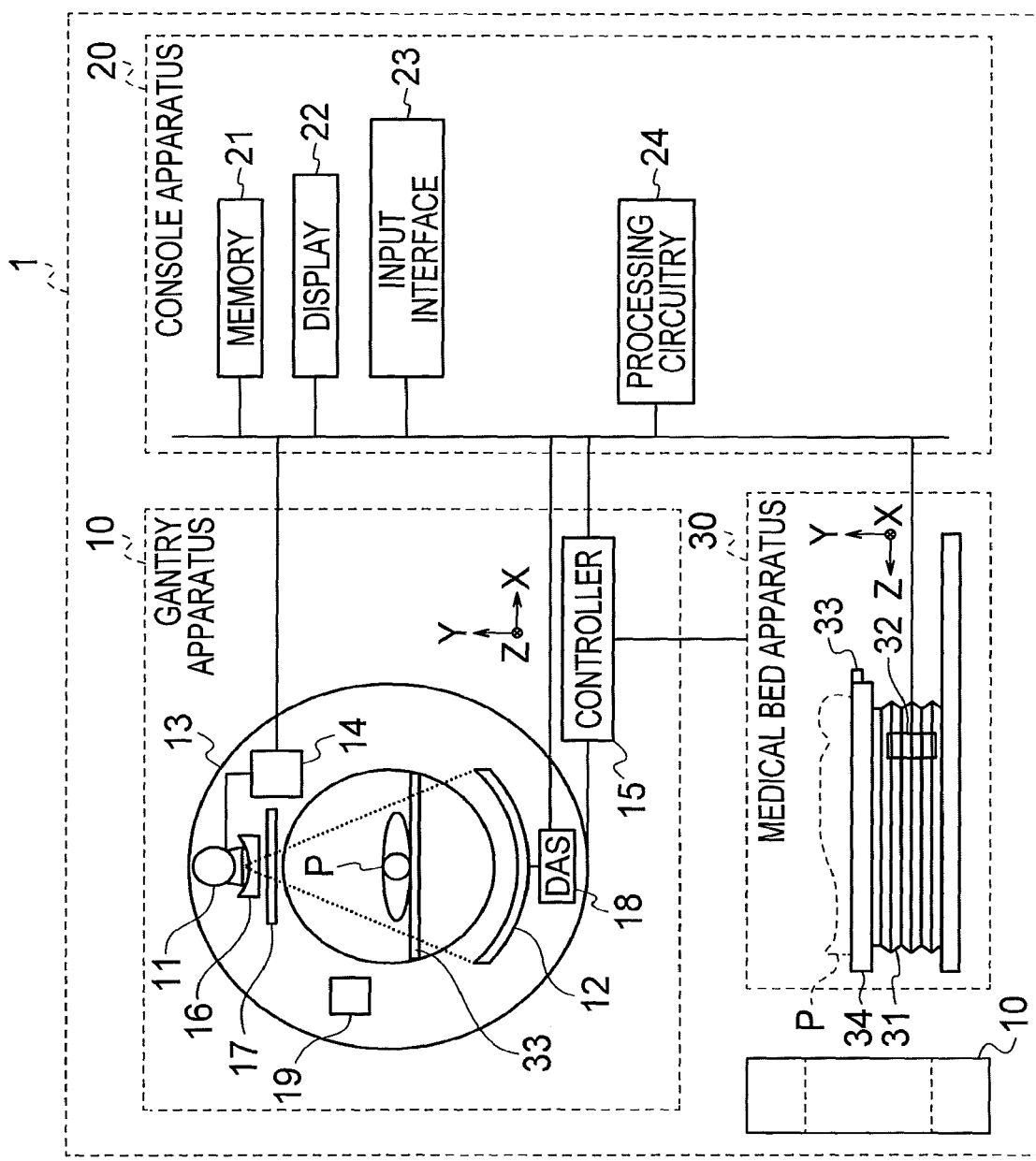
FIG. 1 is a view showing a schematic configuration of an X-ray CT system according to a first embodiment.

FIG. 1 is a view showing a schematic configuration of an X-ray CT system according to a first embodiment. An X-ray CT system 1 according to the present embodiment includes a gantry apparatus 10, a console apparatus 20, and a medical bed apparatus 30.

The gantry apparatus 10 includes an X-ray tube 11, an X-ray detector 12, a rotary frame 13, an X-ray high voltage device 14, a controller 15, a wedge 16, a collimator 17, a data acquisition system (DAS) 18, and a gantry operation panel 19.

The X-ray tube 11 is a vacuum tube in which a thermal electron is radiated from a cathode (a filament) to an anode (a target) by application of a high voltage from the X-ray high voltage device 14, to generate an X-ray.

The X-ray detector 12 detects the X-ray radiated from the X-ray tube 11 and passed through a subject P, and outputs an electric signal corresponding to an X-ray dose to the DAS 18. The rotary frame 13 is an annular frame which supports the X-ray tube 11 and the X-ray detector 12 opposed to each other so that the X-ray tube 11 and the X-ray detector 12 are rotated by the controller 15. The X-ray high voltage device 14 includes a high voltage generator having an electric circuit for a transformer, a rectifier and the like, and having a function of generating the high voltage to be applied to the X-ray tube 11; and an X-ray controller which controls an output voltage in response to the X-ray radiated from the X-ray tube 11.

The controller 15 has a processing circuitry having a central processing unit (CPU) and others, and a drive mechanism including a motor, an actuator and others. The controller 15 has a function of controlling operations of the gantry apparatus 10 and the medical bed apparatus 30 upon receiving an input signal from an input interface 23 attached to the console apparatus 20 or the gantry apparatus 10 as will be described later. Upon receiving the input signal, for example, the controller 15 controls and rotates the rotary frame 13, controls and tilts the gantry apparatus 10, and controls and operates the medical bed apparatus 30 and a top plate 33. Note that the controller 15 may be provided in the gantry apparatus 10 or may be provided in the console apparatus 20.

The wedge 16 is a filter to adjust the dose of the X-ray radiated from the X-ray tube 11.

The collimator 17 is a lead plate or the like to narrow down an irradiation range with the X-ray passed through the wedge 16, and a slit is formed by combination of a plurality of lead plates or the like. The DAS 18 has an amplifier which performs amplification processing to the electric signal output from each X-ray detection element of the X-ray detector 12, and an A/D converter which converts the electric signal to a digital signal, to generate detection data. The detection data generated by the DAS 18 is transferred to the console apparatus 20. The gantry operation panel 19 has an operation button for operating gantry apparatus 10, etc.

The console apparatus 20 has a memory 21, a display 22, the input interface 23, and a processing circuitry 24. The memory 21 stores, for example, projection data and reconstructed image data. The display 22 displays various types of information. For example, the display 22 outputs a medical image (a CT image) generated by the processing circuitry 24, a graphical user interface (GUI) to accept various operations from an operator, and the like. The input interface 23 accepts, from the operator, collection conditions in collecting the projection data, reconstruction conditions in reconstructing the CT image, image processing conditions in generating a post-processed image from the CT image, and the like. The processing circuitry 24 controls an operation of the whole X-ray CT system 1. Note that in the present embodiment, the console apparatus 20 is separate from the gantry apparatus 10, but the gantry apparatus 10 may include the console apparatus 20 or parts of components of the console apparatus 20.

The medical bed apparatus 30 is an apparatus on which the subject P of a scan target is laid and moved. FIG. 1 shows a base 31, a bed drive device 32, the top plate 33, and a support frame 34 as components of the medical bed apparatus 30. Hereinafter, the lateral direction of the top plate 33 which is horizontal to a floor surface on which the X-ray CT system 1 is installed will be referred to as an X-axis direction, an axial direction perpendicular to the X-axis direction and vertical to the floor surface will be referred to as a Y-axis direction, and a longitudinal direction of the top plate 33 which is perpendicular to the X-axis direction and the Y-axis direction will be referred to as a Z-axis direction.

The base 31 is a housing which supports the support frame 34 movably in the Y-axis direction. The bed drive device 32 is a motor or an actuator which moves the top plate 33 on which the subject P is laid, in the Z-axis direction. The top plate 33 provided on an upper surface of the support frame 34 is a plate on which the subject P is laid. The bed drive device 32 may move the support frame 34 in the Z-axis direction, in addition to the top plate 33.

Figure 2:
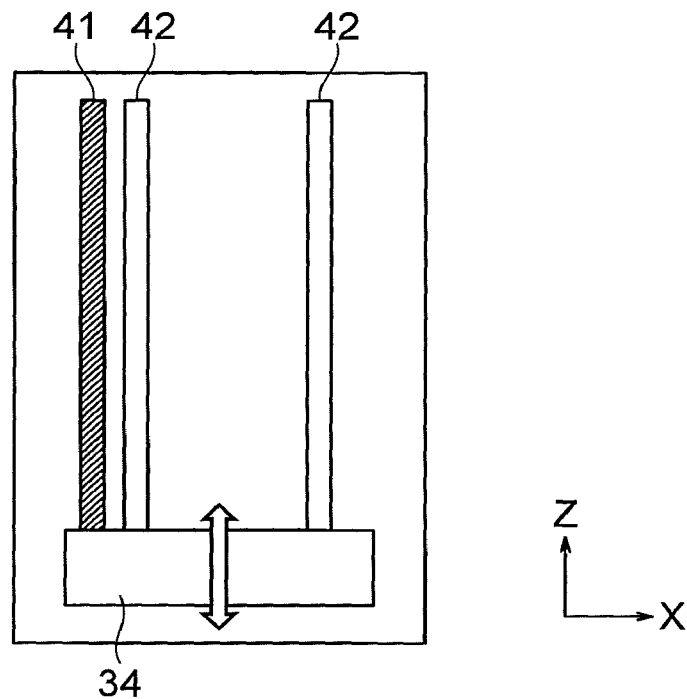
FIG. 2 is a plan view schematically showing one example of a drive mechanism of a support frame.

FIG. 2 is a plan view schematically showing one example of a drive mechanism configured to drive the support frame 34 in the Z-axis direction. This drive mechanism has a ball screw 41 and two linear guides 42. The ball screw 41 and the linear guides 42 extend in the Z-axis direction. The ball screw 41 converts a rotation movement of the bed drive device 32 (see FIG. 1) into a linear movement of the support frame 34. Consequently, the support frame 34 is guided by the linear guides 42 to move in the Z-axis direction. At this time, the top plate 33 coupled to the support frame 34 also moves in the Z-axis direction.

A pair of frames 51 and 52 extends in the Z-axis direction. A pair of covers 53 and 54 is disposed inside the pair of frames 51 and 52, and extends in the Z-axis direction. The pair of covers 53 and 54 is formed, for example, by processing a sheet metal. Here, a structure of a main part of the medical bed apparatus 30 is described in detail with reference to FIG. 3.

Figure 3:
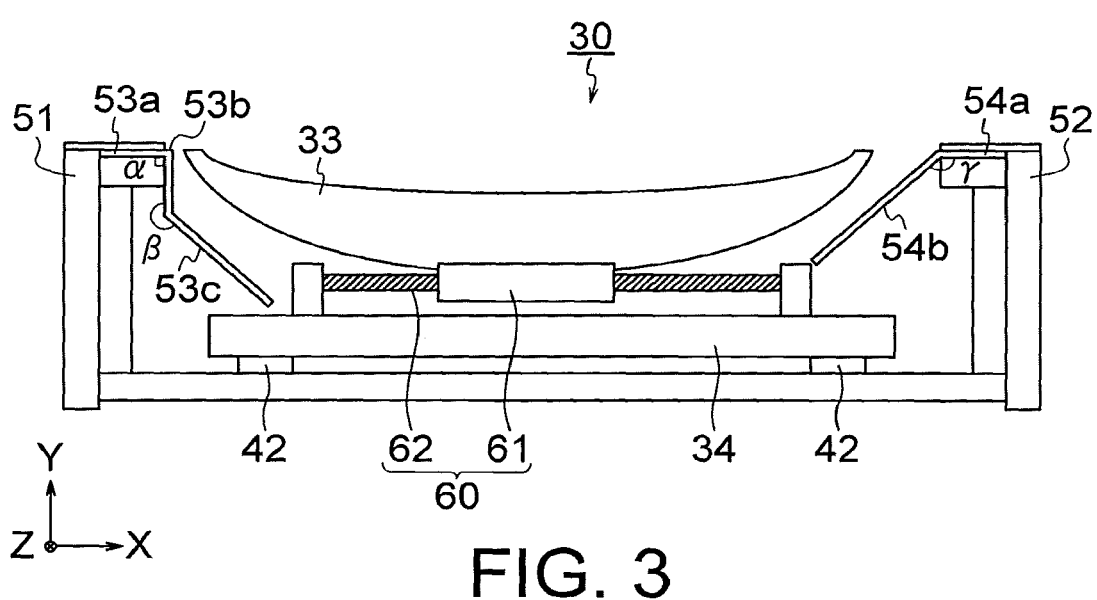
FIG. 3 is a side view of a main part of a medical bed apparatus according to the first embodiment seen from a Z-axis direction.

FIG. 3 is a side view of the main part of the medical bed apparatus 30 seen from the Z-axis direction. As shown in FIG. 3, the pair of frames 51 and 52 is disposed on both sides of the top plate 33 in the X-axis direction. Furthermore, the pair of covers 53 and 54 is provided between the pair of frames 51 and 52 and the top plate 33, respectively.

The cover 53 has a first portion 53a, a second portion 53b, and a third portion 53c. The first portion 53a is provided in the frame 51. Specifically, the first portion 53a is inserted in a gap provided in an upper portion of the frame 51.

The second portion 53b bends downward from the first portion 53a, and is exposed outward from the frame 51. That is, the second portion 53b extends downward from the first portion 53a in the Y-axis direction. Therefore, in the present embodiment, an angle α formed between the first portion 53a and the second portion 53b is a right angle. Furthermore, in the present embodiment, an angle β formed between the second portion 53b and the third portion 53c is an obtuse angle.

On the other hand, the cover 54 has a first portion 54a and a second portion 54b. The first portion 54a is provided in the frame 52. Specifically, the first portion 54a is inserted in a gap provided in an upper portion of the frame 52. The second portion 54b bends obliquely downward from the first portion 54a, and the second portion 54b is exposed outward from the frame 52. That is, the second portion 54b extends obliquely downward from the first portion 54a in the Y-axis direction. Consequently, in the present embodiment, an angle γ formed between the first portion 54a and the second portion 54b is an obtuse angle.

Furthermore, as shown in FIG. 3, the top plate 33 is fixed to a driver 60. The driver 60 drives the top plate 33 in the X-axis direction within such a range that the top plate does not come in contact with the pair of covers 53 and 54. Here, a configuration of the driver 60 is described with reference to FIG. 4.

Figure 4:
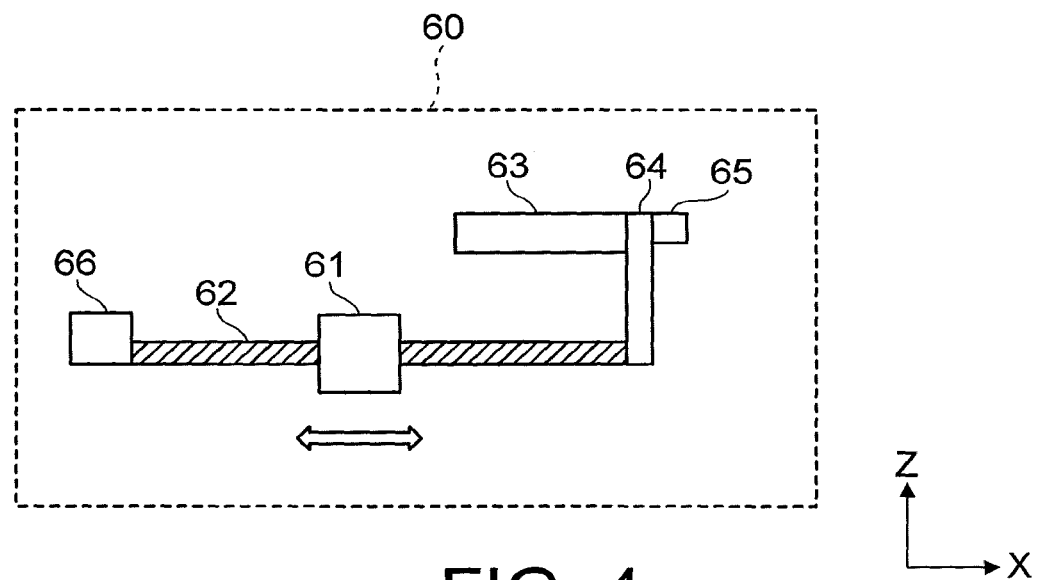
FIG. 4 is a view showing one configurational example of a driver.

FIG. 4 is a view showing one configurational example of the driver 60. The driver 60 shown in FIG. 4 has a block 61, a ball screw 62, a motor 63, a belt 64, an encoder 65, and a brake 66. In the driver 60, when the motor 63 rotates and operates based on the above described control of the controller 15, the belt 64 transmits a rotary force of the motor 63 to the ball screw 62. Consequently, the block 61 attached to the ball screw 62 linearly moves in the X-axis direction. The top plate 33 is coupled to the block 61 (see FIG. 3), so that the top plate 33 can also move in the X-axis direction. A position of the top plate 33 in the X-axis direction corresponds to a rotational position of the motor 63. Consequently, the encoder 65 detects the rotational position of the motor 63, and outputs data of the detected position to the controller 15.

The controller 15 defines the drive range of the top plate 33 in the X-axis direction based on this position data. That is, the controller 15 limits positions of both ends of the top plate 33 in the X-axis direction so that the top plate does not come in contact with the pair of covers 53 and 54.

When the top plate 33 moves to a predetermined position, the brake 66 stops the motor 63 based on the control of the controller 15. Note that when fine positional control is not necessary, the encoder 65 does not have to be provided. Furthermore, the brake 66 may be manual.

Figure 5:
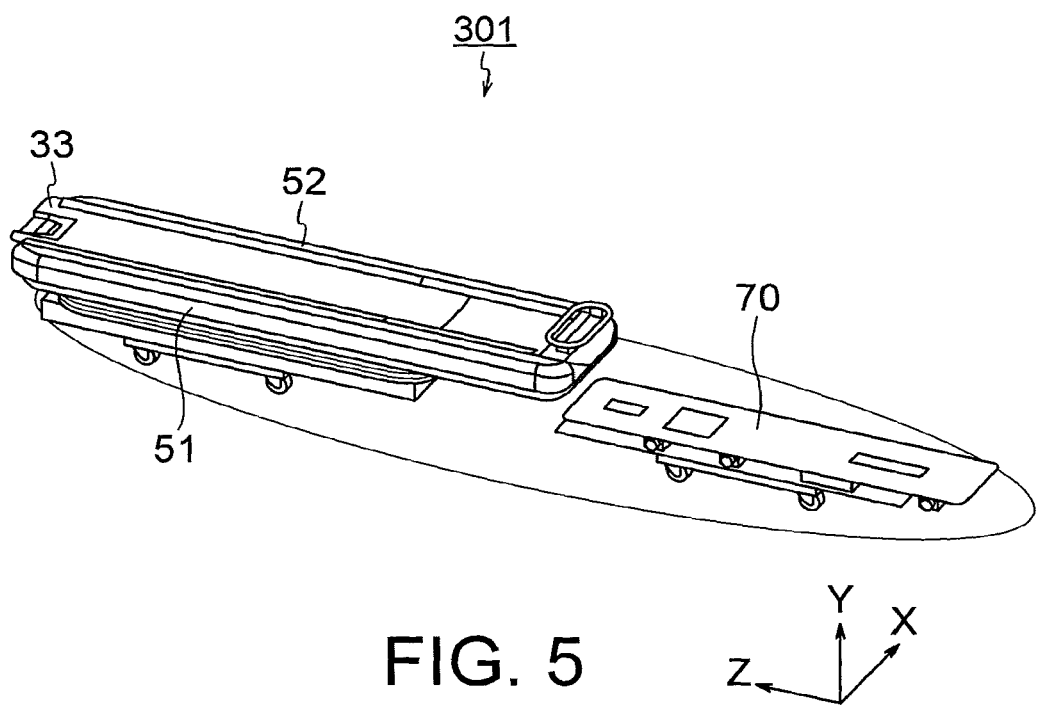
FIG. 5 is a perspective view showing a structure of a medical bed apparatus according to Comparative Example 1.
Figure 6:
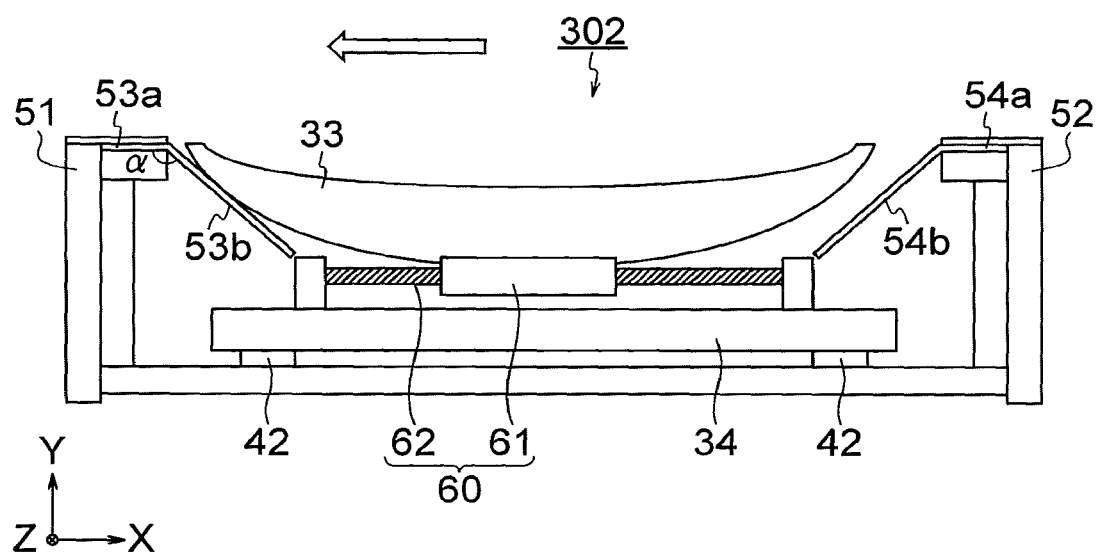
FIG. 6 is a side view showing a structure of a medical bed apparatus according to Comparative Example 2.

Here, there are described Comparative Example 1 and Comparative Example 2 having configurations different from the above described configuration of the medical bed apparatus 30 according to the present embodiment, with reference to FIG. 5 and FIG. 6. Note that in FIG. 5 and FIG. 6, components similar to the above described components of the medical bed apparatus 30 are denoted with the same reference signs, and detailed description is omitted.

First, a medical bed apparatus 301 according to Comparative Example 1 is described with reference to FIG. 5. In the medical bed apparatus 301, a drive unit 70 is attached from outside to undersides of frames 51 and 52. Consequently, the whole medical bed apparatus 301 can move in an X-axis direction that is a lateral direction of a top plate 33.

However, it is necessary for the drive unit 70 to drive the whole medical bed apparatus 301, and a large drive force is therefore required. As a result, time and labor for remodeling and cost burdens increase.

Next, a medical bed apparatus 302 according to Comparative Example 2 will be described with reference to FIG. 6. In the medical bed apparatus 302, a top plate 33 is only moved in an X-axis direction by use of a driver 60 in the same manner as in the present embodiment. The driver 60 may drive only the top plate 33, so that a capacity of a motor 63 (see FIG. 4) can decrease. As a result, time and labor for remodeling and cost burdens can decrease.

However, in the medical bed apparatus 302, an angle α formed between a first portion 53a and a second portion 53b of a cover 53 is an obtuse angle. Consequently, it is presumed that, when the top plate 33 is driven toward a side of the cover 53, the top plate 33 comes in contact with the second portion 53b as shown in FIG. 6. In this case, an accident such as breakage of the top plate 33 might occur, which adversely affects safety.

On the other hand, according to the medical bed apparatus 30 of the above described present embodiment, as shown in FIG. 3, the angle α formed between the first portion 53a and the second portion 53b of the cover 53 is the right angle. That is, the second portion 53b of the cover 53 of the present embodiment bends in a direction away from the top plate 33 differently from the comparative examples. Consequently, the contact of the top plate 33 with the second portion 53b can be avoided while acquiring the drive of the top plate 33 in the X-axis direction. Therefore, it is possible to sufficiently secure the safety during the drive of the top plate.

Figure 7A:
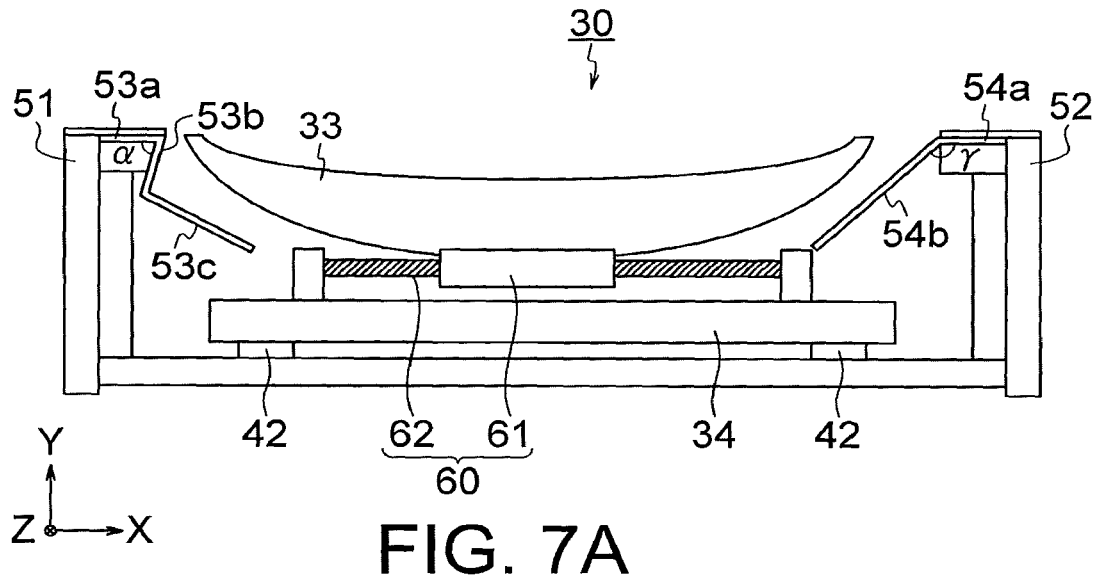
FIG. 7A is a side view showing a modification of a cover.

Note that the angle α formed between the first portion 53a and the second portion 53b is not limited to the right angle, and may be an acute angle as shown in FIG. 7A. Also in this case, a second portion 53b of a cover 53 bends in a direction away from a top plate 33, so that contact of the top plate 33 with the second portion 53b can be avoided.

Figure 7B:
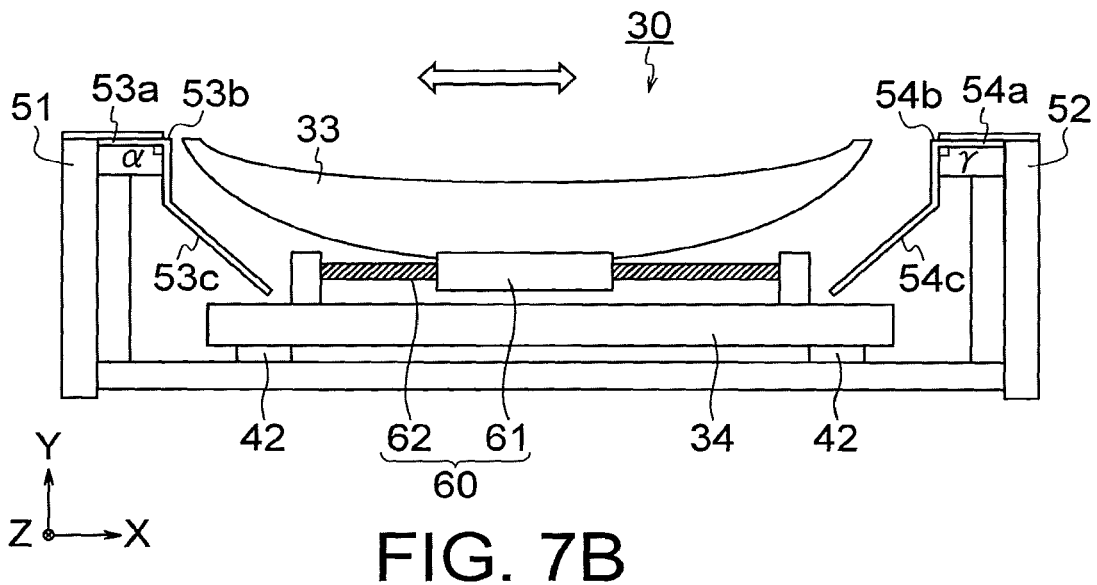
FIG. 7B is a side view showing another modification.

Furthermore, portions corresponding to the first portion 53a, the second portion 53b, and the third portion 53c may be provided in the cover 54 in place of the cover 53. Additionally, as shown in FIG. 7B, a cover 54 may also have a first portion 54a, a second portion 54b, and a third portion 54c, in addition to a cover 53. The first portion 54a, the second portion 54b, and the third portion 54c correspond to a first portion 53a, a second portion 53b, and a third portion 53c of the cover 53, respectively. That is, at least one of a pair of covers 53 and 54 may have the above three portions.

In particular, when both of the pair of covers 53 and 54 include the above three portions, that is, when the pair of covers 53 and 54 has a linearly symmetric shape with respect to a Y-axis direction, a drive range of the top plate 33 can enlarge toward a side of the cover 54. Consequently, it is possible to enlarge a range in which safety is secured.

(Modification 1)

Figure 8A:
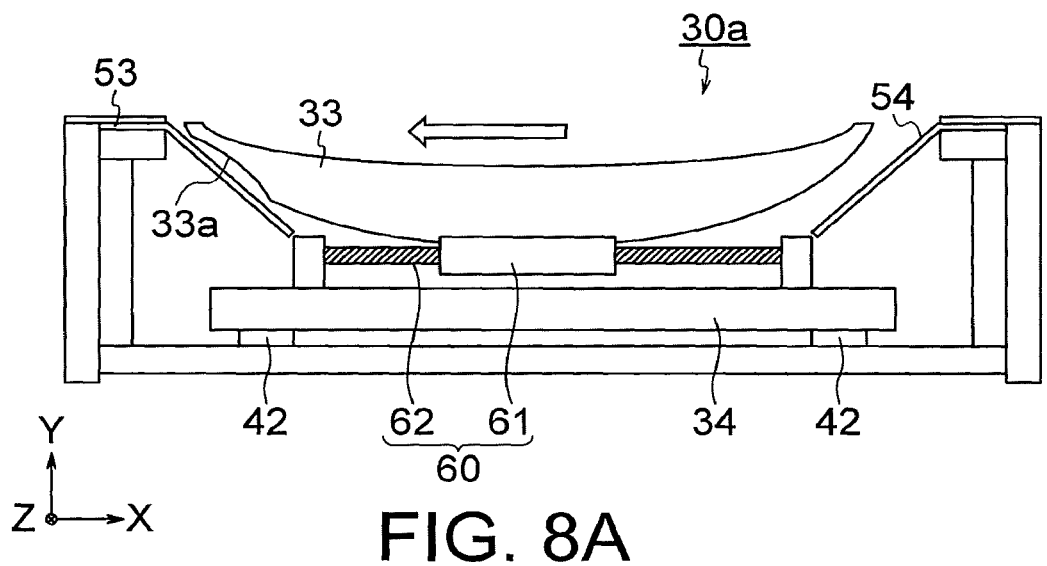
FIG. 8A is a side view of a main part of a medical bed apparatus according to Modification 1 seen from a Z-axis direction.

FIG. 8A is a side view of a medical bed apparatus according to Modification 1 seen from a Z-axis direction. In a medical bed apparatus 30a shown in FIG. 8A, a concave portion 33a is provided in a part of a bottom surface of a top plate 33. As shown in FIG. 8A, the concave portion 33a faces a cover 53 at a position of the top plate 33 which is closest to the cover 53 in a drive range by a driver 60 in an X-axis direction. Consequently, a gap is formed between the top plate 33 and the cover 53, so that contact of the top plate with the cover can be avoided.

Figure 8B:
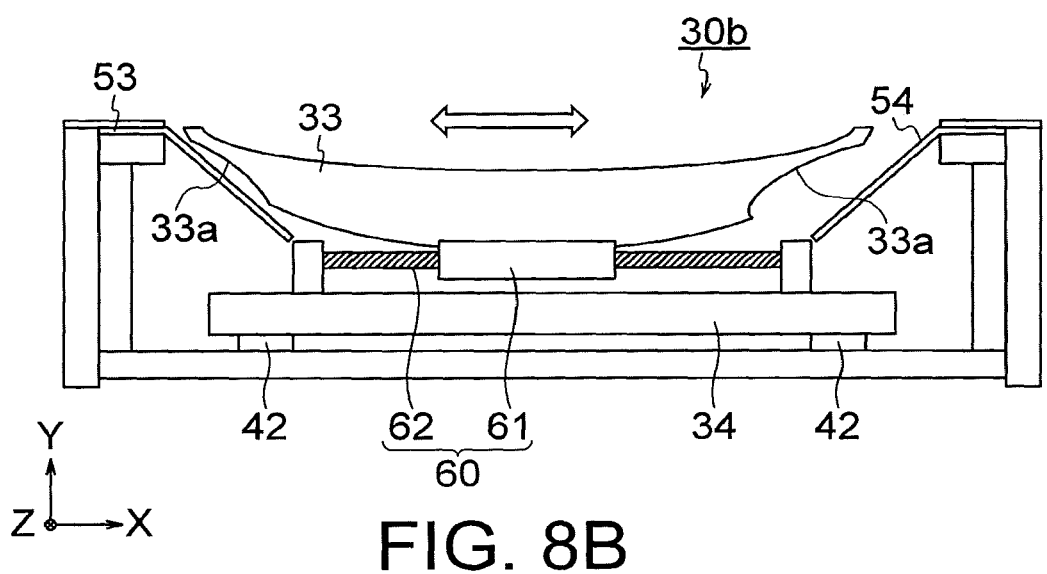
FIG. 8B is a side view of a main part of another medical bed apparatus according to Modification 1 seen from a Z-axis direction.

FIG. 8B is a side view of another medical bed apparatus according to Modification 1 seen from a Z-axis direction. In a medical bed apparatus 30b shown in FIG. 8B, a concave portion 33a is provided in a portion of a bottom surface of a top plate 33 which faces a cover 53, and a concave portion is also provided in a portion of the bottom surface of the top plate which faces a cover 54. Consequently, also when the top plate 33 moves to a position closest to the cover 53, a gap is acquired between the top plate and the cover. Consequently, it is possible to secure safety even when a drive range of the top plate 33 enlarges toward a cover 54 side.

Note that in the present modification, the concave portion 33a is recessed in a curved shape. However, a shape of the concave portion 33a is not limited to the curved shape, and may be, for example, a notch shape as long as the gap can be formed at the position of the top plate 33 which is closest to the cover 53 or the cover 54 in the drive range by the driver 60.

(Modification 2)

Figure 9A:
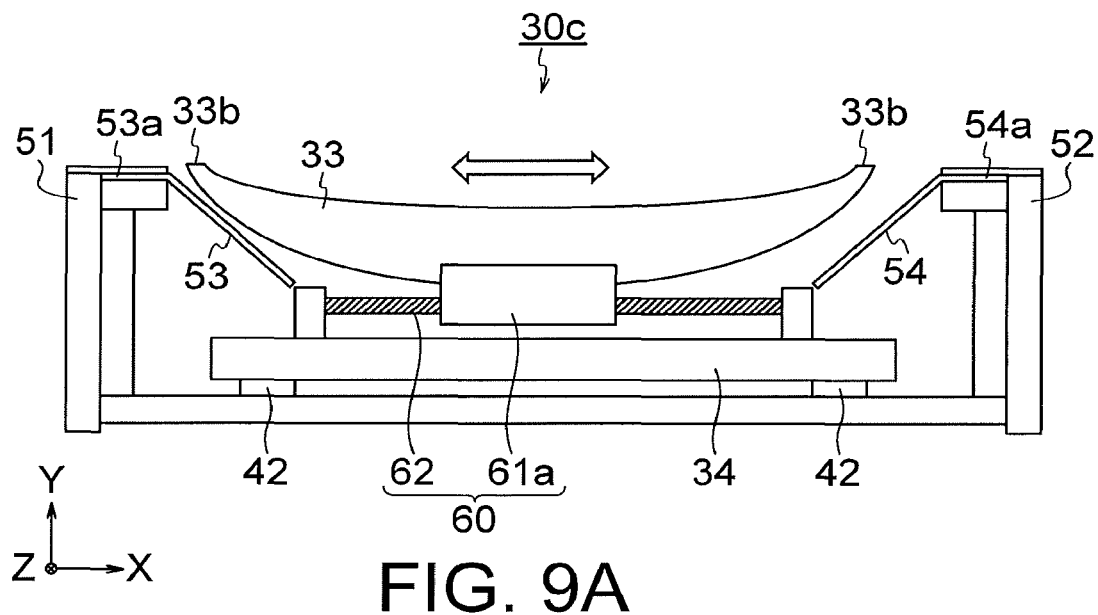
FIG. 9A is a side view of a main part of a medical bed apparatus according to Modification 2 seen from a Z-axis direction.

FIG. 9A is a side view of a main part of a medical bed apparatus according to Modification 2 seen from a Z-axis direction. In a medical bed apparatus 30c shown in FIG. 9A, a driver 60 has a block 61a. A thickness of the block 61a is larger than a thickness of the block 61 described above. Consequently, a position of an upper end 33b of a top plate 33 can be set to be higher than a position of each of upper surfaces 51a and 52a of a pair of frames 51 and 52. Consequently, a gap between the top plate 33 and a pair of covers 53 and 54 enlarges with respect to an X-axis direction. Therefore, contact of the top plate 33 with the pair of covers 53 and 54 can be avoided also when the top plate is driven in the X-axis direction.

Furthermore, according to the present modification, the block 61 may only be replaced with the block 61a, and processing of the top plate 33 or the pair of covers 53 and 54 is not required. Consequently, time and labor for a remodel operation can noticeably decrease. Note that the position of the upper end 33b may be set to the same as the position of each of the upper surfaces 51a and 52a.

Figure 9B:
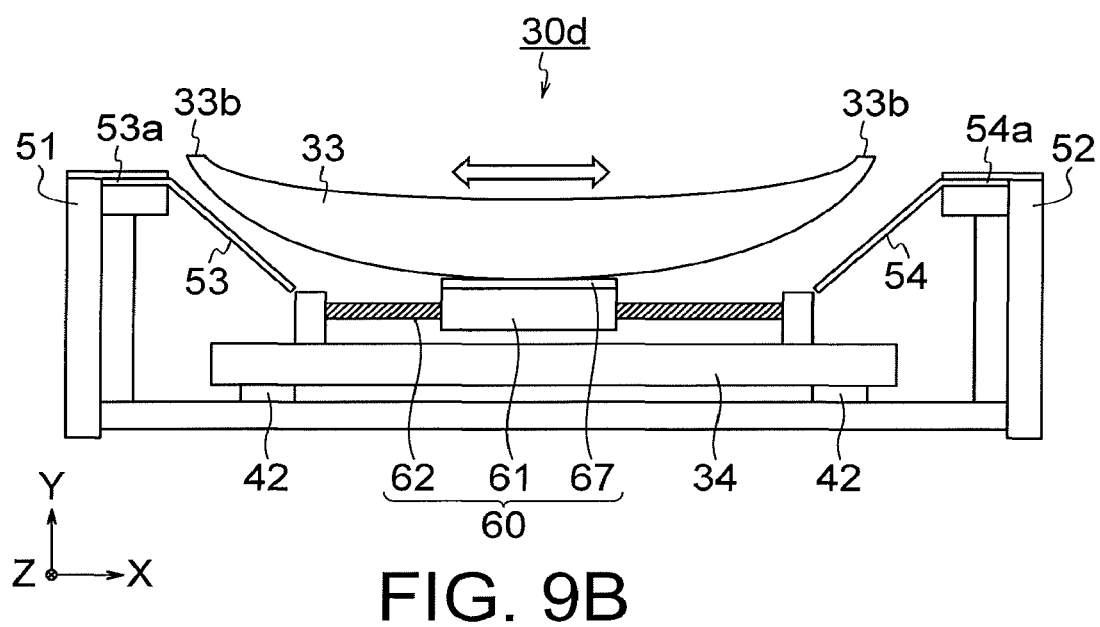
FIG. 9B is a side view of a main part of another medical bed apparatus according to Modification 2 seen from a Z-axis direction.

FIG. 9B is a side view of a main part of another medical bed apparatus according to Modification 2 seen from a Z-axis direction. In a medical bed apparatus 30d shown in FIG. 9B, a spacer 67 is provided between a block 61 and a top plate 33. Also in this case, a position of an upper end 33b of the top plate 33 can be set to be the same as or higher than positions of each of upper surfaces 51a and 52a of a pair of frames 51 and 52.

Also in the present modification, contact of the top plate 33 with a pair of covers 53 and 54 can be avoided, and safety during the drive of the top plate can be secured. Furthermore, also in the present modification, the spacer 67 may only be installed between the block 61 and the top plate 33, so that time and labor for a remodel operation can noticeably decrease.

Second Embodiment

An X-ray CT system according to a second embodiment is different from the X-ray CT system 1 according to the first embodiment in that the system includes a medical bed apparatus 30e in place of the medical bed apparatus 30. Hereinafter, a structure of the medical bed apparatus 30e will be described with reference to FIG. 10.

Figure 10:
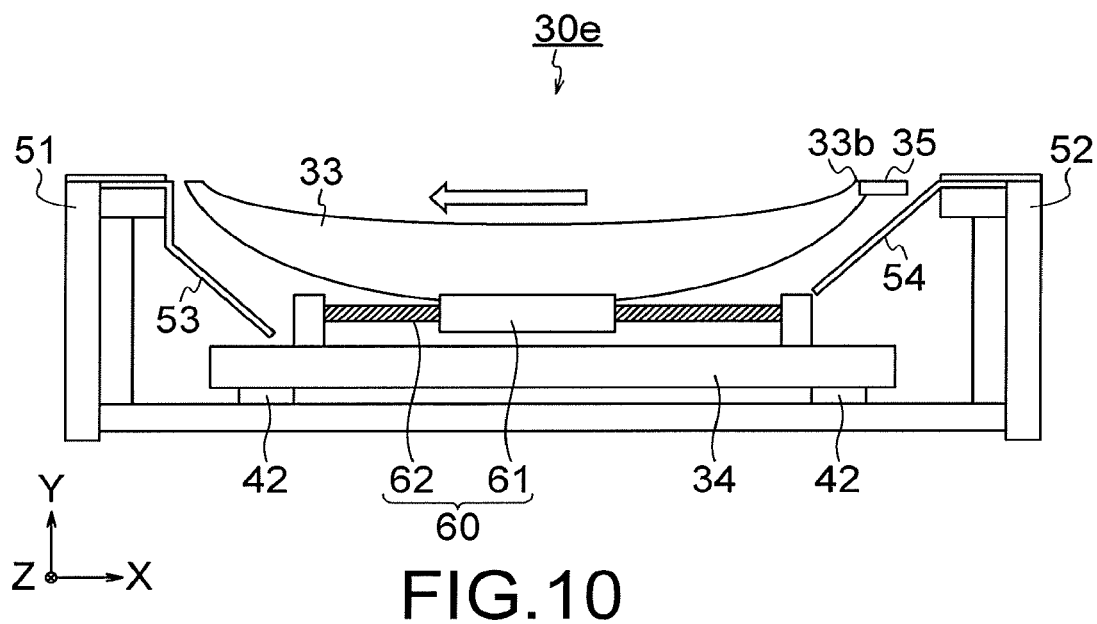
FIG. 10 is a side view of a main part of a medical bed apparatus according to a second embodiment seen from a Z-axis direction.

In the medical bed apparatus 30e shown in FIG. 10, an overhang portion 35 is newly provided in addition to the components of the medical bed apparatus 30. The overhang portion 35 is an elastic member made of, for example, a rubber, and extends outward from an upper end 33b of a top plate 33 toward a cover 54.

As shown in FIG. 10, when the top plate 33 moves toward a cover 53 side, a gap between the top plate 33 and the cover 54 enlarges. In this case, an accident that a finger or the like is caught in this gap might occur. However, in the present embodiment, the overhang portion 35 is attached to the top plate 33, and hence the gap between the top plate 33 and the cover 54 reduces. Consequently, it is possible to improve safety during drive of the top plate.

Figure 11:
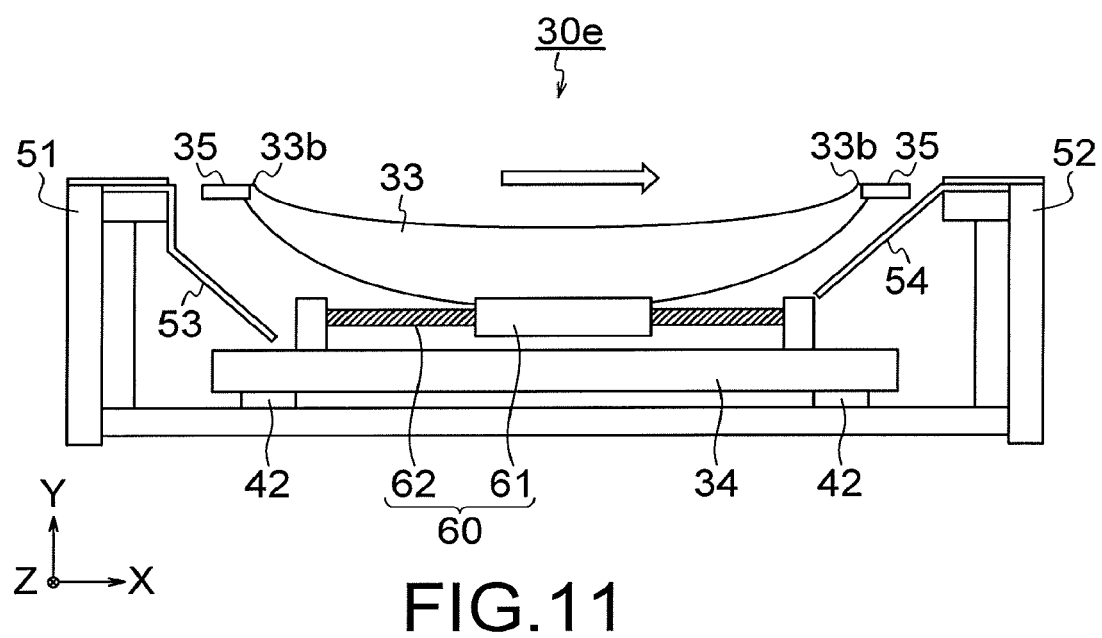
FIG. 11 is a side view showing a modification of an overhang portion.

Note that the overhang portion 35 may be attached to an upper end 33b on a cover 53 side. Furthermore, as shown in FIG. 11, an overhang portion 35 may be provided at an upper end 33b on each side of a pair of covers 53 and 54. That is, the overhang portion 35 may be attached to at least one of the upper ends of the top plate on the sides of the pair of covers 53 and 54.

Particularly in the embodiment where the overhang portions 35 are provided on both the sides of the pair of covers 53 and 54, even when the top plate 33 moves toward the cover 54 side, the gap between the top plate 33 and the cover 53 can be reduced. Consequently, it is possible to further improve the safety during the drive of the top plate. Furthermore, the overhang portion 35 is the elastic member. Consequently, even when the overhang portion 35 comes in contact with the cover 53 or the cover 54, impact generated due to the contact can be mitigated.

Note that the overhang portions 35 may move in conjunction with left and right movement of the top plate 33. In this case, at the top plate 33, the overhang portions 35 can be connected to a driver obtained by miniaturizing the driver 60 shown in FIG. 4, for example. When the operation button of the gantry operation panel 19 is pressed, the controller 15 moves the top plate 33 left and right through the driver 60. At the same time, the controller 15 also moves the overhang portions 35 provided on the opposite side to the moving direction of the top plate 33 to overhang from the top plate 33, through the above mentioned driver.

Consequently, the gap generated by the movement of the top plate 33 can be automatically reduced. Also, as described above, when the overhang portions 35 automatically moves in the opposite direction to the moving direction of the top plate 33, the overhang portions 35 can be a metal sheet, for example. Note that the control function regarding the movement of the overhang portions 35 may be provided in the controller 15 of the gantry apparatus 10, or in the medical bed apparatus 30.

(Modification 3)

Figure 12:
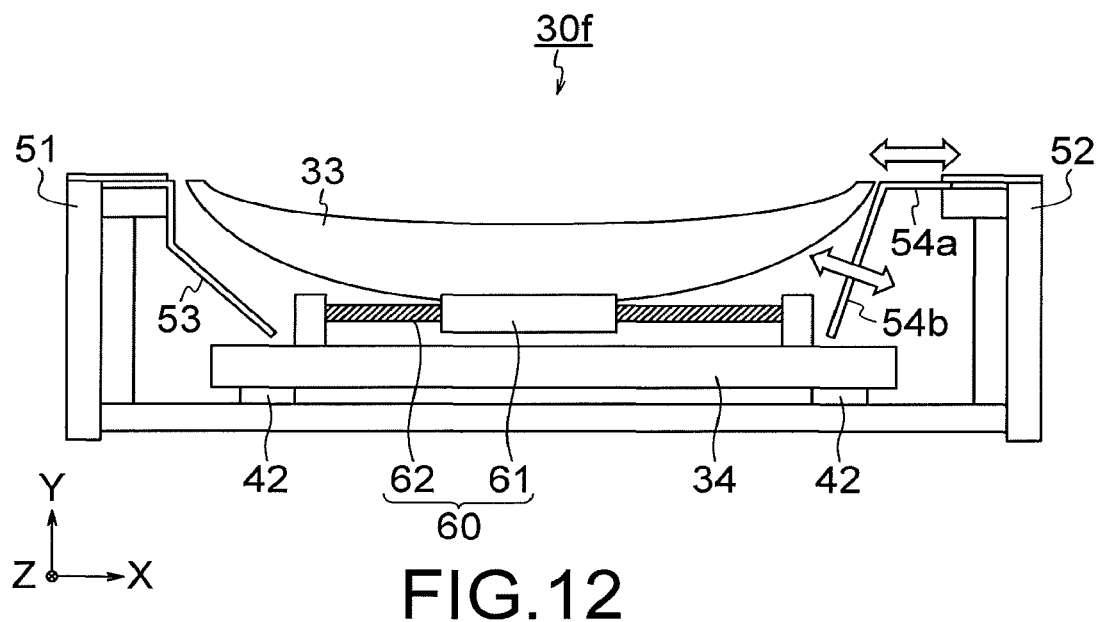
FIG. 12 is a side view of a main part of a medical bed apparatus according to Modification 3 seen from a Z-axis direction.

FIG. 12 is a side view of a main part of a medical bed apparatus according to Modification 3 seen from a Z-axis direction. In a medical bed apparatus 30f shown in FIG. 12, a first portion 54a of a cover 54 is attached to a frame 52 so that the portion is manually movable in a direction parallel to an X-axis direction. Furthermore, a second portion 54b of the cover 54 is coupled to the first portion 54a so that the second portion is manually movable in a direction oblique to the X-axis direction.

According to the present modification, when a top plate 33 moves toward a cover 53 side, the first portion 54a is pulled out from the frame 52 in the X-axis direction, and a gap between the top plate 33 and the cover 54 can be accordingly reduced. Furthermore, tilt of the second portion 54b is adjusted, so that contact of the top plate 33 with the second portion 54b can be avoided.

Therefore, in the same manner as in the second embodiment, even when the top plate 33 moves toward the cover 53 side, it is possible to prevent an accident that a finger is caught in the gap between the top plate 33 and the cover 54, and safety during the drive of the top plate can improve. Note that in the present modification, the cover 53 may be a movable member, and both of a pair of covers 53 and 54 may be movable members. That is, at least one of the pair of covers 53 and 54 may be the movable member.

In particular, when both of the pair of covers 53 and 54 are the movable members and when the top plate 33 moves to one side in the X-axis direction, a gap on the other side in the X-axis direction can be inhibited from being enlarged. Consequently, the safety can further improve.

Note that at least one of the pair of covers 53 and 54 may move in conjunction with left and right movement of the top plate 33. In this case, at the pair of frames 51 and 52, the pair of covers 53 and 54 can be connected to a driver obtained by miniaturizing the driver 60 shown in FIG. 4, for example. When the operation button of the gantry operation panel 19 is pressed, the controller 15 moves the top plate 33 left and right through the driver 60. At the same time, the controller 15 also moves the pair of covers 53 and 54 provided on the opposite side to the moving direction of the top plate 33 in the same direction as the top plate 33, through the above mentioned driver.

Consequently, the gap generated by the movement of the top plate 33 can be automatically reduced. Note that the control function regarding the movement of the pair of covers 53 and 54 may be provided in the controller 15 of the gantry apparatus 10, or in the medical bed apparatus 30.

(Modification 4)

Figure 13:
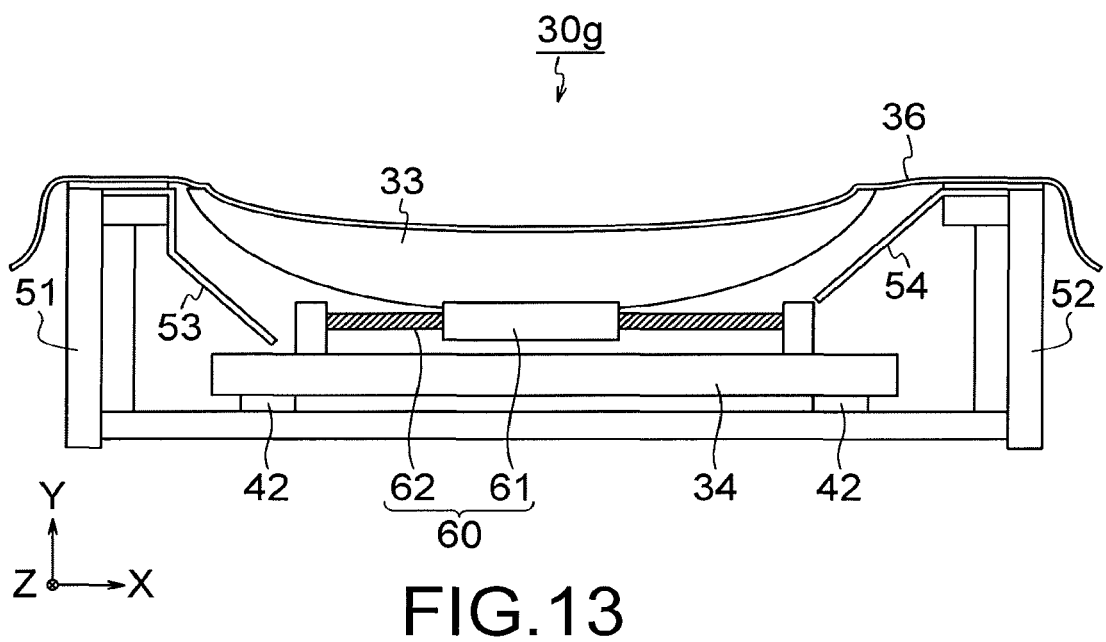
FIG. 13 is a side view of a main part of a medical bed apparatus according to Modification 4 seen from a Z-axis direction.

FIG. 13 is a side view of a main part of a medical bed apparatus according to Modification 4 seen from a Z-axis direction. In a medical bed apparatus 30g shown in FIG. 13, a cover member 36 is provided over an upper surface of a top plate 33 and upper surfaces of a pair of frames 51 and 52. The cover member 36 is made of, for example, nylon.

According to the present modification, the cover member 36 covers a gap between the top plate 33 and a pair of covers 53 and 54. Consequently, even when the top plate 33 moves in an X-axis direction, it is possible to prevent an accident that a finger or the like is caught in the gap between the top plate 33 and the pair of covers 53 and 54. Therefore, safety during drive of the top plate can improve in the same manner as in the second embodiment. Furthermore, in the present modification, the cover member 36 may only be placed over the top plate 33 and the pair of frames 51 and 52, so that time and labor for remodeling and cost burdens can noticeably decrease.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray CT system comprising:
    a gantry rotatably holding an X-ray source and an X-ray detector for CT imaging;
    a top plate on which a subject of the CT imaging is laid, having a length in a longitudinal direction and a lateral direction;
    a driver configured to drive the top plate in a lateral direction of the top plate,
    a support frame movably supporting the top plate, wherein the driver is disposed between the support frame and the top plate to move the top plate relatively to the support frame;
    a pair of side frames provided on both sides of the top plate in the lateral direction, and
    a pair of side covers fixed to both sides of the side frames, and provided between the side frames and the top plate in the lateral direction, wherein
    the top plate and the side covers are arranged so that the top plate does not come in contact with the side covers in a drive range of the top plate by the driver in the lateral direction.

2. The X-ray CT system according to claim 1, wherein at least one of the side covers is attached to the frame so that the cover is movable in a direction away from and towards the top plate.

3. The X-ray CT system according to claim 2, wherein the at least one of the side covers moves in conjunction with left and right movement of the top plate.

4. The X-ray CT system according to claim 1, wherein the at least one of the side covers has a first portion provided in the frame, and a second portion which bends downward from the first portion and is exposed outward from the frame, and an angle formed between the first portion and the second portion is a right angle or an acute angle.

5. The X-ray CT system according to claim 1, further comprising an overhang portion which extends outward from the top plate toward at least one of the side covers.

6. The X-ray CT system according to claim 5, wherein the overhang portion moves in conjunction with left and right movement of the top plate.

7. The X-ray CT system according to claim 5, wherein the overhang portion is an elastic member.

8. The X-ray CT system according to claim 2, wherein the direction is a direction parallel to the lateral direction or oblique to the lateral direction.

9. The X-ray CT system according to claim 1, further comprising a cover member provided over an upper surface of the top plate and upper surfaces of the side frames, and configured to cover each gap between the top plate and the side frames.

10. The X-ray CT system according to claim 4, wherein the at least one of the cover also has a third portion, and an angle formed between the second portion and the third portion is an obtuse angle.

11. The X-ray CT system according to claim 1, wherein the top plate has a concave portion in a bottom surface of the top plate which faces one of the side covers.

12. The X-ray CT system according to claim 11, wherein the concave portion is recessed in a curved shape.

13. The X-ray CT system according to claim 11, wherein the concave portion is provided in a portion of the bottom surface which faces one of the side covers at a position of the top plate which is closest to said one of the side covers in the drive range.

14. The X-ray CT system according to claim 1, wherein the top plate is attached to the driver so that a position of each upper end of the top plate is the same as or higher than a position of each upper surface of the frame.

15. A medical bed apparatus for medical imaging comprising:
    a top plate on which a subject of the medical imaging is laid,
    a driver configured to drive the top plate in a lateral direction of the top plate,
    a support frame movably supporting the top plate, wherein the driver is disposed between the support frame and the top plate to move the top plate relatively to the support frame:
    a pair of side frames provided on both sides of the top plate in the lateral direction, and
    a pair of side covers fixed to both sides of the side frames, and provided between the the side frames and the top plate in the lateral direction, wherein
    the top plate and the side covers are arranged so that the top plate does not come in contact with the side covers in a drive range of the top plate by the driver in the lateral direction.

* * * * *